(12) United States Patent
Grelsamer

(10) Patent No.: US 6,620,199 B2
(45) Date of Patent: Sep. 16, 2003

(54) DEVICE FOR REINFORCING BONE IN PARTIAL KNEE REPLACEMENT SURGERY

(76) Inventor: Ronald P. Grelsamer, 35 E. 85th St., New York, NY (US) 10028

(*) Notice: Subject to any disclaimer, the term of this patent is extended or adjusted under 35 U.S.C. 154(b) by 0 days.

(21) Appl. No.: 09/905,062

(22) Filed: Jul. 13, 2001

(65) Prior Publication Data

US 2003/0014121 A1 Jan. 16, 2003

(51) Int. Cl.[7] .................................................. A61F 2/38
(52) U.S. Cl. ......................................................... 623/20.32
(58) Field of Search ........................... 623/18.11, 20.32, 623/20.21, 20.28, 20.3, 20.34; 606/72; A61F 2/38

(56) References Cited

U.S. PATENT DOCUMENTS

| | | | |
|---|---|---|---|
| 4,865,607 A | 9/1989 | Witzel et al. | |
| 5,047,058 A | 9/1991 | Roberts et al. | |
| 5,092,895 A | * 3/1992 | Albrektsson et al. | ......... 623/20 |
| 5,176,710 A | 1/1993 | Hahn et al. | |
| 5,180,383 A | * 1/1993 | Haydon | ....................... 606/72 |
| 5,201,768 A | 4/1993 | Caspari et al. | |
| 5,344,458 A | 9/1994 | Bonutti | |
| 5,370,693 A | * 12/1994 | Kelman et al. | ................ 623/16 |
| 5,489,311 A | * 2/1996 | Cipolletti | ....................... 623/20 |
| 5,534,032 A | 7/1996 | Hodorek | |
| 5,549,687 A | 8/1996 | Coates et al. | |
| 5,749,875 A | * 5/1998 | Puddu | ........................... 606/87 |
| 5,782,924 A | * 7/1998 | Johnson | ........................ 623/20 |
| 6,008,433 A | 12/1999 | Stone | |
| 6,099,531 A | * 8/2000 | Bonutti | ........................ 606/87 |
| 6,102,954 A | * 8/2000 | Albrektsson et al. | .......... 623/20 |
| 6,245,110 B1 | * 6/2001 | Grundei et al. | ........... 623/20.31 |
| 6,348,053 B1 | * 2/2002 | Cachia | ......................... 606/72 |
| 2002/0022890 A1 | * 2/2002 | Jacobsson et al. | ........ 623/18.11 |

* cited by examiner

Primary Examiner—David H. Willse
Assistant Examiner—Javier G. Blanco
(74) Attorney, Agent, or Firm—John P. White; Cooper & Dunham LLP

(57) ABSTRACT

A partial knee replacement device comprises a reinforcing spike which spans the tibia and supports a tibial inset. The spike has a pointed tip, shaft and head. The spike when driven across the cross-section of the tibia has its tip engaging the peripheral edge of the tibial hard bone, and its head supported by the opposite peripheral edge of the tibial hard bone.

18 Claims, 2 Drawing Sheets

DEVICE FOR REINFORCING BONE IN PARTIAL KNEE REPLACEMENT SURGERY

BACKGROUND OF THE INVENTION

The present invention relates to knee replacement devices, and more particularly to partial knee replacement devices.

Knee replacements generally fall into two categories, total or partial. Partial knee replacement are also referred to as unicompartmental. Both total and partial knee replacements address arthritis and related conditions of the knee.

Partial or unicompartmental replacements fall into two categories, those that cover the tibial (shin) bone, and those that are inset within it.

The inset type comprises an inset which is implanted within the top of the tibia within the core of the bone with the result that the implant rests on potentially soft bone, because the core of the bone is softer than its periphery. An advantage of this type of implant is that it can be inserted through a relatively small incision thus speeding a patient's recovery time. However, one of the disadvantages of the implant is that the implant may sink into the soft bone core over time through use.

SUMMARY OF THE INVENTION

In accordance with the present invention, a reinforcement for a partial knee implant device is provided.

According to one aspect of the invention, a partial knee replacement device is provided, comprising a tibial inset adapted to be inserted into the soft bone area in the top of the tibia, and a reinforcing member which is adapted to span the tibia and support the tibial inset.

According to another aspect of the invention, a partial knee replacement device is provided, comprising a tibial inset adapted to be inserted in the soft bone area in the top of the tibial, and a reinforcing spike having a pointed tip, shaft and head which spans the tibia and supports the tibial inset.

According to another aspect of the invention, a reinforcement device for a partial knee replacement inset is provided, comprising a reinforcing member which is adapted to span the tibia from side to side and support a tibial inset.

DETAILED DESCRIPTION OF THE PREFERRED EMBODIMENT

According to one aspect of the invention, a partial knee replacement device is provided, comprising an inset adapted to be inserted into the soft bone area in the top of the tibia, and a reinforcing member which is adapted to span the tibia and support the inset.

The reinforcing member is preferably broad and flat in cross-section.

The reinforcing member is preferably a spike having a tip, a shaft and a head. The spike tip is preferably pointed.

The spike head preferably has at least one protrusion, and preferably two, each protrusion having a ring shape.

According to another aspect of the invention, a partial knee replacement device is provided, comprising a tibial inset adapted to be inserted in the soft bone area in the top of the tibia, and a reinforcing spike having a pointed tip, shaft and head for spanning the tibia and supporting the inset.

According to another aspect of the invention, a reinforcement device for a partial knee replacement inset is provided, comprising a reinforcing member which is adapted to span the tibia from side to side and support a tibial inset.

Figure 1:
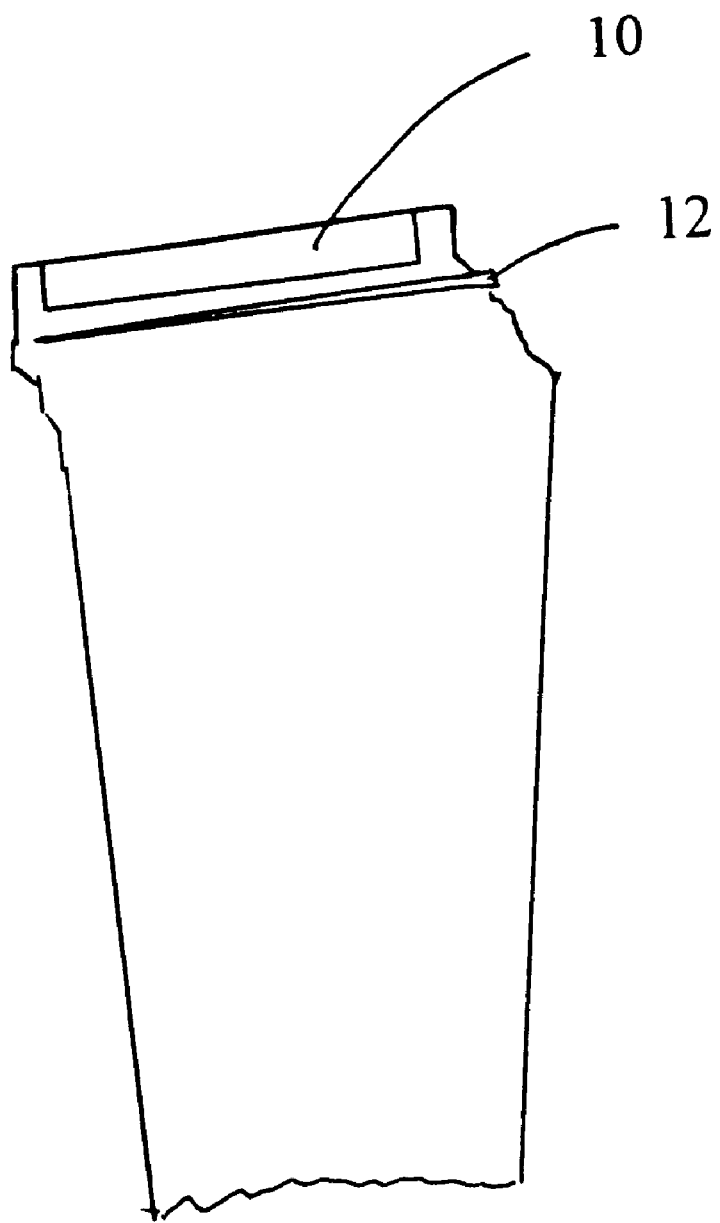
FIG. 1 is a side view, in cross section, of a tibia and the reinforced knee inset according to the invention.
Figure 2:
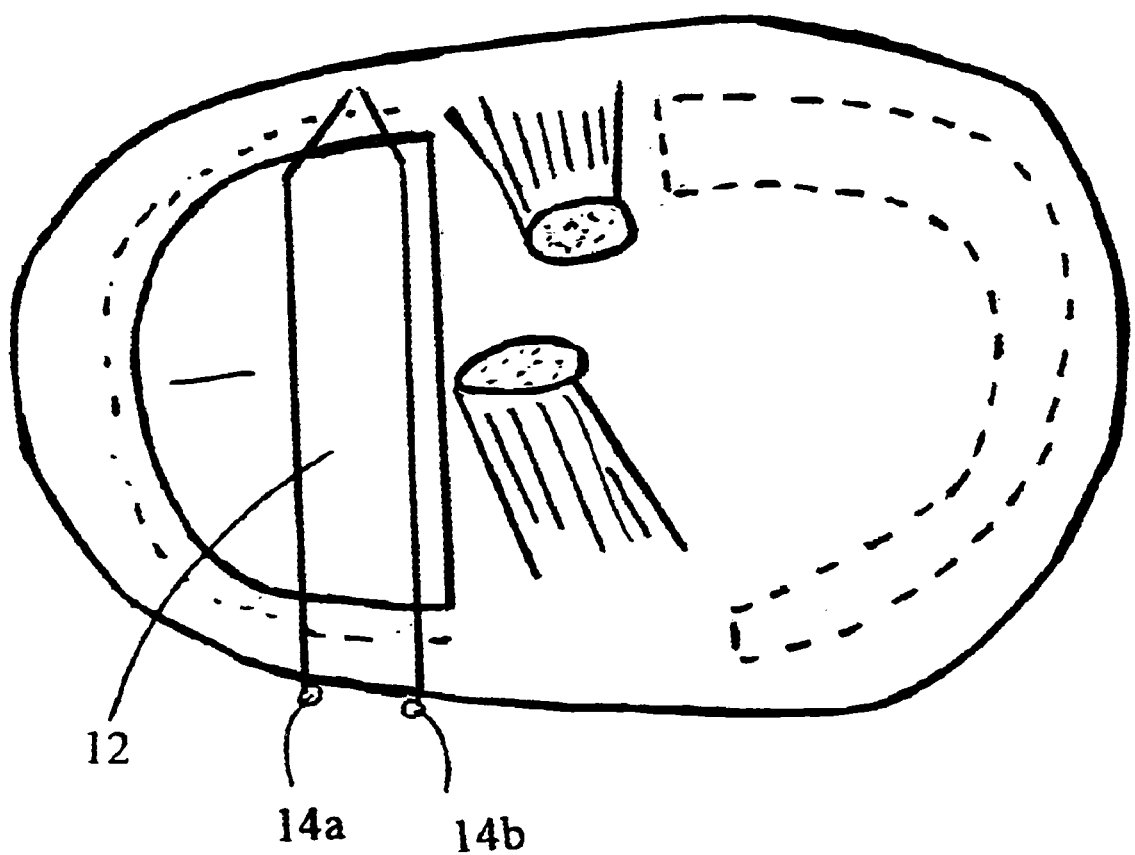
FIG. 2 is a top plan view of a tibia showing the reinforcing member and reinforced knee inset according to the invention.

As shown in FIGS. 1 and 2, the preferred embodiment according to the invention comprises an inset 10 and a reinforcing member 12. The reinforcing member is in the form of a spike which spans the soft bone of the tibia, and is anchored on the near side and far side into the stronger harder peripheral tibial bone. The spike is preferably pointed at its tip, and may be either tapered or of substantially uniform cross section along its length. The spike may be broad and flat in cross-section. The head of the spike preferably has two protrusions 14a and 14b in the shape of small rings, which aid in gripping the spike should it need to be later extracted.

The implant and spike are made of biocompatible material which are available in the art. The spike may be made of stainless steel carbon or similar material.

As shown in FIG. 2, the tip of the spike pierces and engages the peripheral portion of the tibia, shown roughly in dotted lines. More than one spike may be provided. The shape of the spike or spikes may differ from that shown in the preferred embodiment.

Although one embodiment has been shown and described, numerous variations and modifications will readily occur to those skilled in the art. The scope of the invention is defined only by way of the appended claims.

I claim:

1. A partial knee replacement device, consisting essentially of an inset adapted to be inserted into and across substantially the entire soft bone area in the top of the tibia such that the top of the inset is generally level with the top of the hard peripheral bone and does not extend above the top of the hard peripheral bone, and a reinforcing member which is adapted to span the tibia and support the inset.

2. The device according to claim 1, wherein the reinforcing member is relatively broad and flat in cross-section.

3. The device according to claim 1, wherein the reinforcing member is a spike having a tip, a shaft and a head.

4. The device according to claim 3, wherein the spike tip is pointed.

5. The device according to claim 3, wherein the spike head has at least one protrusion.

6. The device according to claim 5, wherein the protrusion has a ring shape.

7. The device according to claim 5, wherein the spike head has two protrusions.

8. A partial knee replacement device consisting essentially of an inset adapted to be inserted in and across substantially the entire soft bone area in the top of the tibia such that the top of the inset is generally level with the top of the hard peripheral bone and does not extend above the top of the hard peripheral bone, and a reinforcing spike having a pointed tip, shaft and head for spanning the tibia and supporting the inset.

9. The device according to claim 8, wherein the protrusion has a ring shape.

10. The device according to claim 9, wherein the protrusion has a ring shape.

11. The device according to claim 9, wherein the spike head has two protrusions.

12. A bone joint replacement device comprising an inset adapted to be inserted into and across substantially the entire soft bone area in the end of a bone such that the inset is substantially totally received in the soft bone area and enclosed on its perimeter by hard peripheral bone and does not extend above the top of the hard peripheral bone, and a reinforcing member which is adapted to span the bone from side to side and support the inset.

13. The device according to claim 12, wherein the reinforcing member is relatively broad and flat in cross-section.

14. The device according to claim 12, wherein the reinforcing member is a spike having a tip, a shaft and a head.

15. The device according to claim 14, wherein the spike tip is pointed.

16. The device according to claim 14, wherein the spike head has at least one protrusion.

17. The device according to claim 16, wherein the protrusion has a ring shape.

18. The device according to claim 16, wherein the spike head has two protrusions.

* * * * *